(12) United States Patent
Bunel et al.

(10) Patent No.: US 6,750,362 B2
(45) Date of Patent: Jun. 15, 2004

(54) PROCESS FOR MAKING 5-FORMYLVALERONITRILE USING REACTIVATED CATALYST

(75) Inventors: Emilio E. Bunel, Carmel, IN (US); Marisa Bonilla, Bear, DE (US); Ronnie Ozer, Arden, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 241 days.

(21) Appl. No.: 10/096,781

(22) Filed: Mar. 12, 2002

(65) Prior Publication Data

US 2003/0176720 A1 Sep. 18, 2003

(51) Int. Cl.$^7$ ............................................. C07C 255/00
(52) U.S. Cl. ...................................................... 558/353
(58) Field of Search .......................................... 558/353

(56) References Cited

U.S. PATENT DOCUMENTS

| | | | |
|---|---|---|---|
| 5,986,126 A | 11/1999 | Bunel et al. | |
| 6,307,107 B1 * | 10/2001 | Bunel et al. | 568/454 |
| 6,372,939 B1 * | 4/2002 | Bunel et al. | 562/553 |
| 6,515,161 B1 * | 2/2003 | Kreutzer et al. | 558/353 |

OTHER PUBLICATIONS

Horvath et al. Chemical Reviews 1991, NMR Under High Gas Pressure, vol. 81, Issue 7, pp. 1339–1351.

* cited by examiner

Primary Examiner—Robert Gerstl

(57) ABSTRACT

Process for making 5FVN, comprising contacting in a reactor 3PN with CO and hydrogen in the presence of a catalyst, the catalyst comprising recycled catalyst that is reactivated using hydrogen.

3 Claims, 2 Drawing Sheets

PROCESS FOR MAKING 5-FORMYLVALERONITRILE USING REACTIVATED CATALYST

BACKGROUND

The hydroformylation of 3-pentenenitrile (3PN) to 5-formylvaleronitrile (5FVN) is an attractive route to produce nylon intermediates. As disclosed in U.S. Pat. No. 5,986,126, the reductive amination of 5FVN produces 6-aminocapronitrile and/or hexamethylenediamine, which are two key intermediates for the production of Nylon-6 and Nylon-6,6 respectively. The oxidation of 5FVN to 5-cyanovaleric acid, followed by hydrogenation to 6-aminocaproic acid, produces caprolactam, which is the monomer of choice to make Nylon-6.

A key element in the overall scheme is a stable catalyst that produces 5FVN by hydroformylation of 3PN. Typical catalysts involved in these reactions comprise a metal, such as rhodium, and an organic ligand, such as a bidentate phosphite. Such catalysts tend to deactivate upon recycle due to irreversible reactions believed to involve the metal center or the ligands coordinated to the metal center. In the case of hydroformylation of 3PN to 5FVN, the most active and selective catalysts comprise bidentate phosphite ligands.

When the hydroformylation of 3PN to 5FVN is performed in a continuous fashion, involving catalyst recycle, the catalyst loses activity continuously.

There is a need in the art, therefore, for making 5FVN in which the inactive form of the catalyst is reactivated.

SUMMARY OF THE INVENTION

This need is met by the present invention, which is a process for making 5FVN, comprising contacting in a reactor 3PN with CO and hydrogen in the presence of a catalyst comprising rhodium and a bidentate phosphite ligand to produce a product stream comprising 5FVN, unreacted 3PN and catalyst, separating at least a portion of said product stream into a low boiler fraction comprising 3PN and a major portion of the 5FVN and a high boiler fraction comprising a minor portion of the 5FVN and catalyst, contacting at least a portion of said high boiler fraction with hydrogen at a temperature in the range 50 degrees C. to 170 degrees C. and a pressure in the range 50 psig to 2000 psig to produce a hydrogen-treated high boiler fraction, and introducing at least a portion of said hydrogen-treated high boiler fraction into the reactor.

BRIEF DESCRIPTION OF THE DRAWING

The drawing consists of two figures.

DETAILED DESCRIPTION OF THE INVENTION

Figure 1:
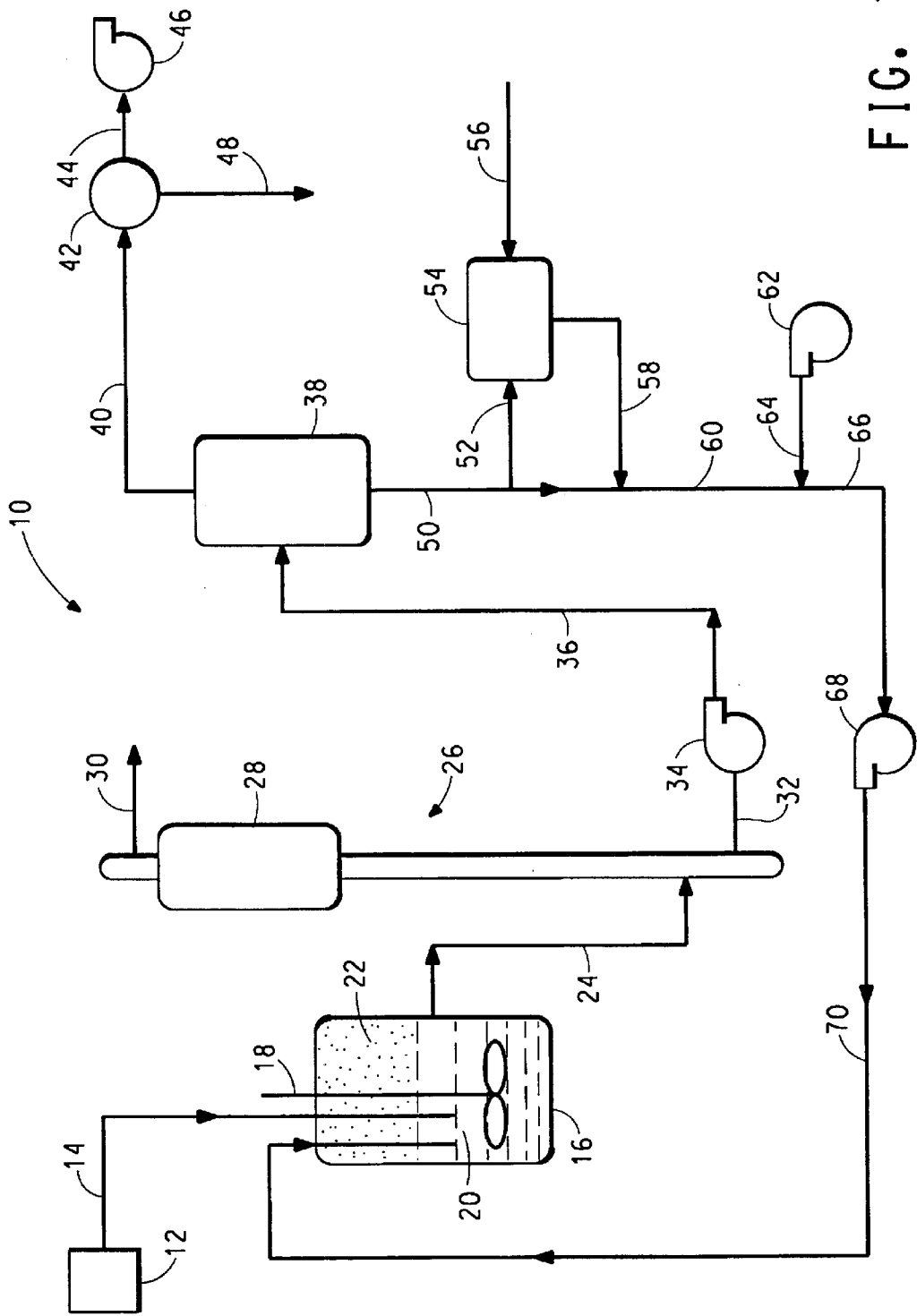
FIG. 1 shows a block diagram depicting apparatus for carrying out the present process.

The use of in-situ NMR spectroscopy has allowed the monitoring of the composition of the catalyst stream as a function of time. The use of this technique permitted the quantitative measurement of the concentration of ligand (Structure I), the resting state of the catalyst (Structure II) and in addition the formation of an inactive form of the catalyst (Structure III). The inactive form of the catalyst corresponds to a cyanide complex of Structure III. A possible theory for the formation of the inactive catalyst is that the catalyst metal center reacts with 3PN to give a crotyl hydrido cyanide complex that eliminates butadiene and hydrogen to give the inactive form of the catalyst.

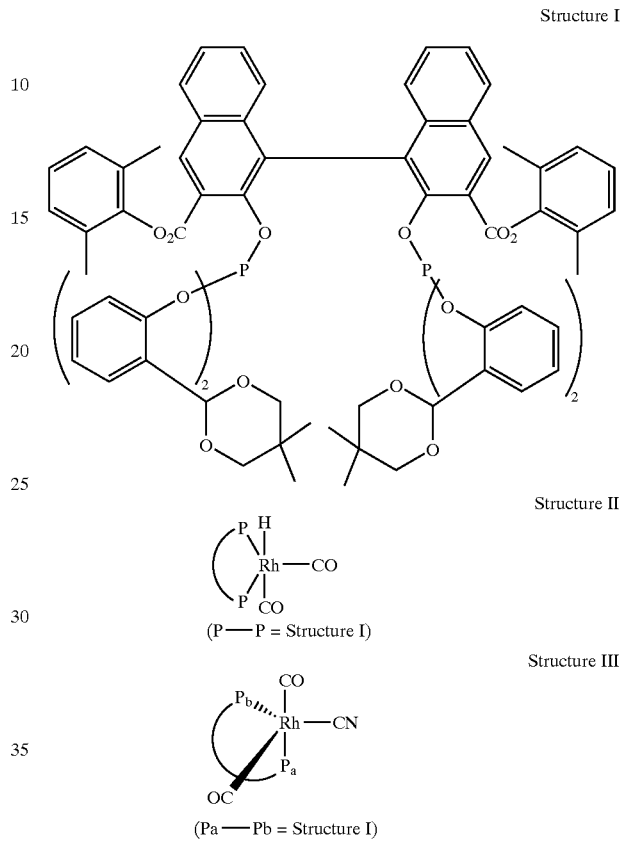

The NMR values for Structure III are shown below:

Rh: $^{103}$Rh=−580.7 ppm $P_a$: $^{31}P_a$=132.7 ppm ($J_{Rh,P}$=206 Hz; $J_{Pa,Pb}$=283 Hz; $J_{P,13C}$=27 Hz)

$P_b$: $^{31}P_b$=131.1 ppm ($J_{Rh,P}$=211 Hz; $J_{Pa,Pb}$=283 Hz; $J_{P,13C}$=27 Hz)

$^{13}$CN: $^{31}$C=112.7 ppm ($J_{Rh,C}$=61 Hz; $J_{P,13C}$=27 Hz)

Referring now to the Drawing, there is shown apparatus 10 for carrying out the present process. A mass flow meter 12 delivers a gas comprising carbon monoxide (CO) and hydrogen (H2) (preferably at a 1:1 ratio) via tubing 14 to a stirred tank reactor 16 containing an agitator 18. The reactor 16 contains a liquid portion 20 that comprises 5FVN, 3PN, valeronitrile and catalyst, as well as some dissolved CO and hydrogen. The catalyst can be present at a concentration between 50 and 500 ppm. Suitable catalysts are complexes of rhodium with bidentate phosphites, such as those disclosed in U.S. Pat. No. 5,986,126. Preferred ligands are those having the structure below:

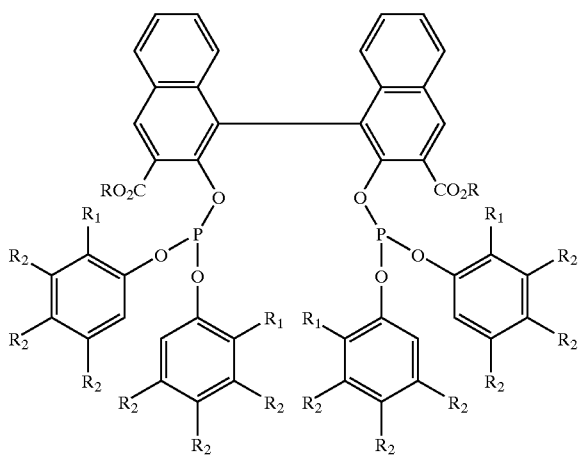

wherein:
R is $C_1$ to $C_{12}$ alkyl or $C_6$ to $C_{20}$ aryl;
$R^1$ is $C_1$ to $C_{12}$ alkyl, $C_6$ to $C_{20}$ aryl, F, Cl, —CO2R, —CH(OR)$_2$, or —CH(OCH$_2$CRRCH$_2$O); and
$R_2$ is H, $C_1$ to $C_{12}$ alkyl, or $C_6$ to $C_{20}$ aryl.

Most preferred ligands have the structure shown below:

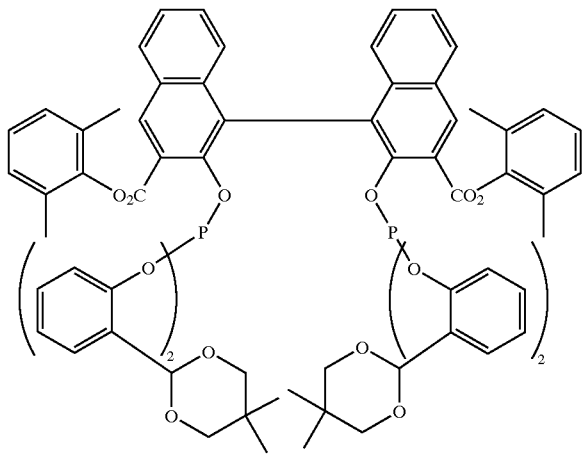

The most preferred catalyst is a catalyst in which rhodium metal is complexed with the ligand of Structure I. The temperature of the reactor can be between about 85 and 105 degrees C., preferably 95 degrees C. when catalyst having ligand of Structure I is used. The pressure in the reactor can be between 35 and 95 psig, preferably 65 psig when catalyst having ligand of Structure 1 is used. Above the liquid portion 20 is a gas portion 22 that comprises CO and hydrogen. Exiting the reactor 16 is take-off line 24 that transports the liquid contents of reactor 16 to a gas/liquid separator 26 that comprises a condenser 28. The gas/liquid separator operates at atmospheric pressure. The condenser 28 receives a gas comprising CO and hydrogen, and duct 30 releases some of this gas from the system. Separator tails line 32 transports the liquid contents 20 (with the gas components substantially removed) to evaporator feed pump 34, which, in turn, pumps the material through feed line 36 to evaporator 38. Evaporator 38 operates at high vacuum, about 3 mm Hg, and at about 95 degrees C. In evaporator 38 the material is separated by evaporation to form a low-boiler fraction (comprising 3PN and a major portion of the 5FVN) that is transported by line 40 to a condenser 42 that converts most of the vapor into a liquid. Vacuum pump 46 withdraws vapor from condenser 42 via line 44. A liquid distillate line 48 withdraws condensed low-boiler material, the desired product of the process, from the condenser 42. High-boiler take-off line 50 removes high boiler material (comprising a minor portion of the 5FVN and catalyst) from condenser 42. A portion of the high boiler material is diverted via line 52 to a catalyst reactivator 54 into which hydrogen is introduced through line 56. The reactivator 54 can be operated at a temperature between 50 and 170 degrees C. and a pressure between 50 and 2000 psig pressure. Reactivated catalyst formed in reactivator 54 is removed through line 58 and mixed with the contents of line 50 in line 60. The contents of line 60 are mixed with 3PN that is introduced through line 64 using feed pump 62. The resulting mixture is fed by line 66 into a catalyst recycle pump 68 back into stirred tank reactor 16.

EXAMPLES

Example 1

General Procedure

3-Pentenenitrile was hydroformylated to 5-formylvaleronitrile in a reactor system that consisted of a 500 ml stainless steel autoclave with a vertically mounted agitator system, a gas sparger for introduction of a mixture of carbon monoxide and hydrogen (1/1 mole ratio) underneath a dual impeller agitator shaft and a liquid dip tube for excess gas and liquid drawoff. The autoclave was heated by an electric band heater, and the internal temperature was controlled by a water-cooled coil inside the autoclave. A liquid feed to the reactor consisted of a mixture of fresh 3-pentenenitriles (substrate) and recycle 5-formylvaleronitrile, higher boilers, and catalyst (complex of rhodium and ligand of Structure I) which came from the bottom of a short hold-up time evaporator (described below). This mixture of recycle material and fresh substrate is fed into the autoclave through a dip tube that ends at the lower impeller for improved mixing. The stream of carbon monoxide and hydrogen and liquid product exiting the reactor was flashed from 95 C. and 3.3 bar to room temperature and 1 bar through a valve that opened into a gas liquid separator vessel. The gas stream passes through a chilled condenser for removal of nitriles from the venting vapor stream. The level of liquid in the separator was controlled and fed via a positive displacement pump to a rolling film evaporator. The evaporator operated at hold-up times of less than 1 minute at 95 degrees C. and 5 mbar. The lower boilers from this evaporator feed, a mixture comprising pentenenitriles, valeronitrile, and formylvaleronitriles (products), was condensed in a chilled condenser and collected in a distillate vessel for analysis. The high boiling stream exiting the evaporator, consisting of primarily formylvaleronitriles and catalyst, was collected in a tails vessel where it was mixed with a continuous feed of fresh 3-pentenenitrile prior to recycle to the hydroformylation reactor. The mixture was then pumped back to the reactor using a positive displacement recycle pump. A ligand addition pump was connected to the reactor feed line so that a solution of ligand and toluene could be added continuously to make up for ligand that had degraded in the above operations. This system permitted continuous feed of 3-pentenenitriles and continuous production of formylvaleronitriles from a single charge of dissolved catalyst.

The hydroformylation reaction was conducted by charging to the reactor, gas-liquid separator, and tails vessel about 1 liter of a catalyst precursor solution of the following composition: 250 to 500 ppm rhodium prepared from rhodium dicarbonyl acetylacetonate, about 1.0 weight percent of Ligand of Structure I (about 1.4 equivalents of ligand per mole of rhodium), the balance being trans 3-pentenenitrile (and low levels of other isomers). The entire system was thoroughly purged of air prior to introduction of the solution. As controlled flows of carbon monoxide and hydrogen (1/1 mole ratio) were fed to the autoclave to maintain 65 psig, liquid flow was started in the recycle loop. The liquid flow was calibrated to provide about 2 hours of space time in the autoclave. The autoclave was heated to 95 C. rapidly and controlled in that temperature for the remainder of the operation. The material was recycled in the loop for 6 hours to achieve greater than 80% conversion of the charged 3-pentenenitriles to formylvaleronitriles. Once these high conversion levels were achieved, the evaporator was heated to 95 degrees C. using a hot oil bath at 125 degrees C., and the pressure in the evaporator was lowered to 4.5 mbar. Fresh 3-pentenenitriles were fed to the recycle line exiting the evaporator in order to maintain system inventory and keep catalyst concentration relatively constant. A mixture of ligand and toluene was also fed to this stream in varying amounts in order to maintain an excess of ligand to rhodium in the reactor. A sample for NMR analysis was removed periodically to check the level of excess ligand and the concentration of the active and inactive catalysts. The analysis was done in a high pressure tube as described in Chemical Reviews 1991, 91(7), 1339–1351, in the presence of 500 psi of CO/H2 (1/1 mole ratio).

The operation described above proceeded for 200 hours of continuous operation with steady production throughout this time. Ligand in toluene and 3-pentenenitrile were added continuously through this period, and a mixture of formylvaleronitriles and pentenenitriles was collected as overhead in the evaporator. At the end of the operation, the tails line of the evaporator (prior to ligand addition, but after 3-pentenenitriles addition ("reactor feed solution")) was drained to a nitrogen purged vessel for storage. The reactor and gas-liquid separator contents were drained to a separate vessel ("reactor contents"). NMR analysis of these solutions showed no active catalyst in the reactor feed solution, whereas the reactor contents showed a mixture of inactive and active catalyst in solution. Table 1, below, shows the concentrations of active and inactive form of catalyst as a function of time, 3PN conversion and 5FVN selectivity as a function of time, and finally the first order rate constant, k, as a function of time.

TABLE 1

Catalyst performance For Example 1

| Hours | Active Catalyst* Structure II | Inactive Catalyst* Structure III | Ligand* Structure II | 3PN Conversion | Selectivity 5FVN | k (1/min) |
|---|---|---|---|---|---|---|
| 11 | 0.0017 | 0.0006 | 0.0000 | 68.74 | 62.32 | 0.018 |
| 23 | 0.0015 | 0.0009 | 0.0000 | 64.48 | 82.60 | 0.015 |
| 47 | 0.0013 | 0.0014 | 0.0000 | 62.99 | 85.46 | 0.014 |
| 69 | 0.0011 | 0.0016 | 0.0002 | 58.47 | 83.74 | 0.012 |
| 95 | 0.0013 | 0.0014 | 0.0008 | 59.15 | 83.25 | 0.012 |
| 112 | 0.0016 | 0.0013 | 0.0012 | 61.53 | 83.16 | 0.013 |
| 136 | 0.0016 | 0.0018 | 0.0017 | 63.45 | 83.82 | 0.014 |
| 160 | 0.0016 | 0.0017 | 0.0019 | 59.99 | 82.50 | 0.012 |
| 184 | 0.0016 | 0.0018 | 0.0020 | 56.15 | 83.23 | 0.012 |
| 208 | 0.0008 | 0.0018 | 0.0018 | 55.78 | 81.88 | 0.011 |

*mmoles/g sample

Example 2

Activity Prior to Reactivation

A 68.63 g of "reactor contents" from Example 1 containing 47.8% of 3-pentenitrile was combined with 1.41 g of o-dichlorobenzene ("ODCB" internal standard for GC) and loaded into a 100 ml autoclave. The autoclave was pressurized with 68 psig of CO/H2 (1/1 mole ratio), heated to 95 degrees C. while CO/H2 was fed at a rate of 40 cc/min. The rhodium concentration determined by X-ray fluorescence (XRF) was 406 ppm. Samples were taken from the autoclave as a function of time to determine the concentration of 3-pentenenitrile.

Example 3

Activity After Reactivation

A 68.71 g of "reactor contents" from Example 1 containing 47.8% of 3-pentenitrile was combined with 1.49 g of o-dichlorobenzene (internal standard for GC) and loaded into a 100 ml autoclave. The rhodium concentration determined by XRF was 410 ppm. The autoclave was pressurized with 300 psig of H2 and heated to 95 degrees C. Hydrogen was vented slowly every 30 minutes and replenished with fresh hydrogen over the course of one hour. The contents of the autoclave were transferred to a distillation apparatus under anaerobic conditions, and the valeronitrile was distilled. The mother liquor containing the catalyst (17.22 g) was combined with 34.89 g of 3-pentenenitrile and 1 g of o-dichlorobenzene under nitrogen and loaded back into the autoclave. The autoclave was pressurized with 66 psig of CO/H2 (1/1 mole ratio), heated to 95 degrees C. while CO/H2 was fed at a rate of 40 cc/min. The rhodium concentration determined by XRF was 330 ppm. Samples were taken from the autoclave as a function of time to determine the concentration of 3-pentenenitrile. Table 2, below, shows 3PN concentration as a function of time for Examples 2 and 3.

TABLE 2

Catalyst performance for Examples 2 and 3

| Time [min] | [3PN]* Example 2 | [3PN]* Example 3 |
|---|---|---|
| 0 | 15.69 | 26 |
| 15 | 14.62 | 19.993 |
| 30 | 12.39 | 15.43 |
| 45 | 11.39 | 12.81 |
| 60 | 9.7 | 11.09 |

*mmoles 3PN/g ODCB

Figure 2:
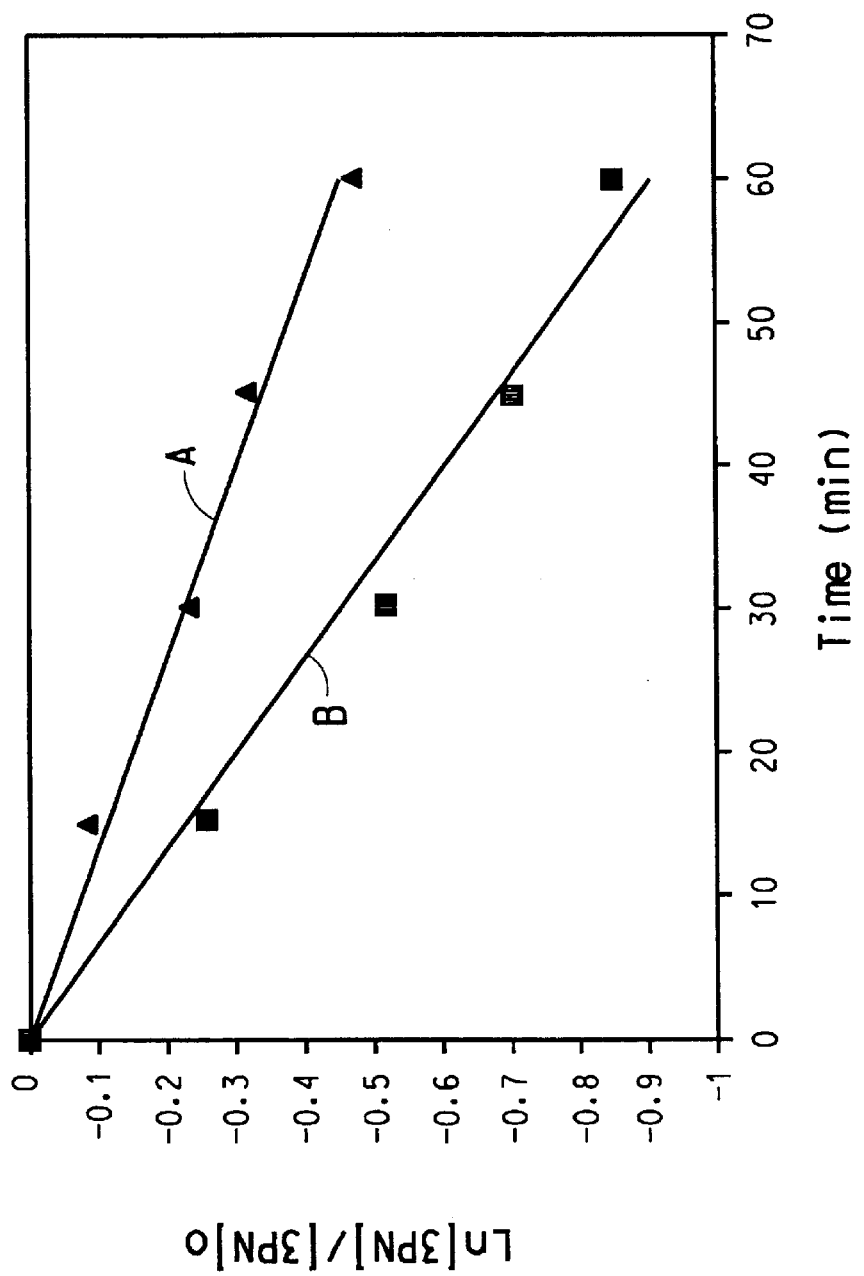
FIG. 2 is a graph showing rate data for Examples 2 and 3.

FIG. 2 shows first order rate data for Examples 2 and 3. The line labeled "A" depicts rate data pertaining to Example 2 and shows a rate constant of 0.0076 $min^{-1}$ and an $R^2$ value of 0.9796. The line labeled "B" depicts rate data pertaining to Example 3 and shows a rate constant of 0.0152 $min^{-1}$ and an $R^2$ value of 0.9793.

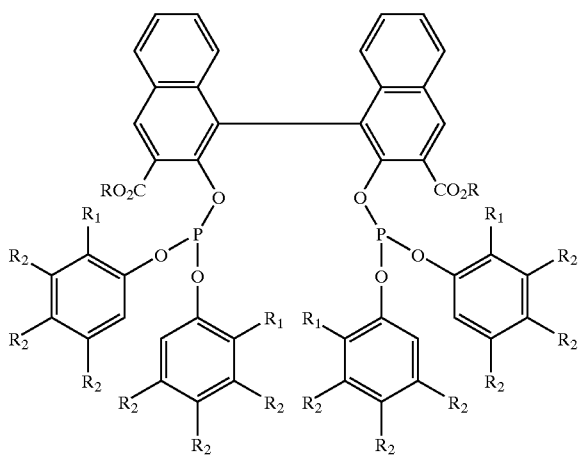
wherein:
R is $C_1$ to $C_{12}$ alkyl or $C_6$ to $C_{20}$ aryl;
$R^1$ is $C_1$ to $C_{12}$ alkyl, $C_6$ to $C_{20}$ aryl, F, Cl, —CO2R, —CH(OR)$_2$, or —CH(OCH$_2$CRRCH$_2$O); and
$R_2$ is H, $C_1$ to $C_{12}$ alkyl, or $C_6$ to $C_{20}$ aryl.
3. The process of claim 2 in which the ligand is a compound of the formula:
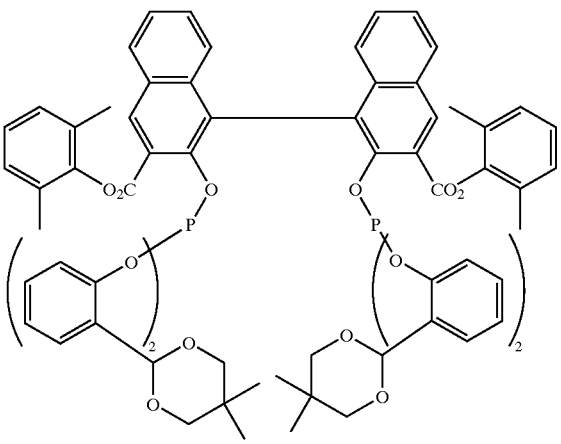

What is claimed is:

1. A process for making 5FVN, comprising contacting in a reactor 3PN with CO and hydrogen in the presence of a catalyst comprising rhodium and a bidentate phosphite ligand to produce a product stream comprising 5FVN, unreacted 3PN and catalyst, separating at least a portion of said product stream into a low boiler fraction comprising 3PN and a major portion of the 5FVN and a high boiler fraction comprising a minor portion of the 5FVN and catalyst, contacting at least a portion of said high boiler fraction with hydrogen at a temperature in the range 50 degrees C. to 170 degrees C. and a pressure in the range 50 psig to 2000 psig to produce a hydrogen-treated high boiler fraction, and introducing at least a portion of said hydrogen-treated high boiler fraction into the reactor.

2. The process of claim 1 in which the ligand is a compound of the formula: